United States Patent
Lee et al.

(10) Patent No.: US 10,933,086 B2
(45) Date of Patent: Mar. 2, 2021

(54) COMPOSITION FOR PREVENTING, ALLEVIATING, OR TREATING ARTHRITIS OR OSTEOPOROSIS, CONTAINING NEOAGAROOLIGOSACCHARIDE

(71) Applicant: DYNEBIO INC., Seongnam-si (KR)

(72) Inventors: Je Hyeon Lee, Seongnam-si (KR); Eun Joo Kim, Seongnam-si (KR); Kyoung Woon Kim, Seoul (KR)

(73) Assignee: DYNEBIO INC., Seongnam-si (KR)

(*) Notice: Subject to any disclaimer, the term of this patent is extended or adjusted under 35 U.S.C. 154(b) by 33 days.

(21) Appl. No.: 16/345,082

(22) PCT Filed: Oct. 17, 2017

(86) PCT No.: PCT/KR2017/011436
§ 371 (c)(1),
(2) Date: Apr. 25, 2019

(87) PCT Pub. No.: WO2018/080077
PCT Pub. Date: May 3, 2018

(65) Prior Publication Data
US 2019/0275075 A1    Sep. 12, 2019

(30) Foreign Application Priority Data
Oct. 27, 2016    (KR) .......................... 10-2016-0140731

(51) Int. Cl.
| | |
|---|---|
| *A61K 31/729* | (2006.01) |
| *A23L 29/30* | (2016.01) |
| *A23L 33/125* | (2016.01) |
| *A61P 19/02* | (2006.01) |
| *A61K 31/702* | (2006.01) |
| *C12P 19/04* | (2006.01) |
| *A23L 33/10* | (2016.01) |

(52) U.S. Cl.
CPC ............ *A61K 31/729* (2013.01); *A23L 29/30* (2016.08); *A23L 33/10* (2016.08); *A23L 33/125* (2016.08); *A61K 31/702* (2013.01); *A61P 19/02* (2018.01); *C12P 19/04* (2013.01)

(58) Field of Classification Search
None
See application file for complete search history.

(56) References Cited

U.S. PATENT DOCUMENTS

2018/0055872 A1* 3/2018 Lee ................ C12Y 207/01107

FOREIGN PATENT DOCUMENTS

| JP | 2007269636 A | * 10/2007 | ........... A61K 31/702 |
|---|---|---|---|
| KR | 10-2014-0061272 A | 5/2014 | |
| KR | 10-2016-0020457 A | 2/2016 | |
| KR | 10-2016-0083329 A | 7/2016 | |
| WO | WO-2016108394 A1 | * 7/2016 | .............. C12P 19/00 |

OTHER PUBLICATIONS

Kudo, O., Sabokbar, A., Pocock, A., Itonaga, I., Fujikawa, Y., & Athanasou, N. A. (2003). Interleukin-6 and interleukin-11 support human osteoclast formation by a RANKL-independent mechanism. Bone, 32(1), 1-7. (Year: 2003).*
Uyangaa Temuujin, et al., "Overexpression and biochemical characterization of DagA from *Streptomyces coelicolor* A3(2): an endotype β-agarase producing neoagarotetraose and neoagarohexaose", Applied Microbiology Biotechnology, 2011, pp. 749-759, vol. 92.
Fu-Jin Wang, et al., "Composition of Two Seaweed-Oligosaccharide-Lysates Derived From Agarase AS-II and Their Ferrous-Chelating Antioxidant Power", Journal of Marine Science and Technology, 2011, pp. 557-564, vol. 19, No. 5.
International Search Report for PCT/KR2017/011436 dated Jan. 31, 2018 (PCT/ISA/210).
Communication dated Jan. 23, 2020, from the Japanese Patent Office in Application No. 2019-540500.
Jpn, J. Rehabill, 2012, vol. 49, No. 10 p. 690-693 (5 Pages Total).
Jpn, J. Rehabill, 2012, vol. 49, p. 683-689 (8 Pages total).

* cited by examiner

*Primary Examiner* — Dale R Miller
(74) *Attorney, Agent, or Firm* — Sughrue Mion, PLLC

(57) ABSTRACT

Provided in the present invention is a novel use of composition containing a neoagarooligosaccharide mixture as an active ingredient. The neoagarooligosaccharide mixture and the like as an active ingredient of the composition according to the present invention can reduce the expression of RANKL, an osteoclast inducer, or IL-6, an inflammatory cytokine, and effectively inhibit differentiation of monocytes into osteoclasts. Thus, the composition according to the present invention may be used as a medicine or functional food for preventing, alleviating, or treating arthritis (especially rheumatoid arthritis). Further, the active ingredient of the composition according to the present invention can be obtained by an enzyme reaction between a readily available substrate such as agar or agarose and DagA as a beta-agarase derived from *Streptomyces coelicolor*. Thus, it can be produced at a relatively low cost and can easily be ingested by anyone because it has no side effects.

5 Claims, 7 Drawing Sheets

Specification includes a Sequence Listing.

SEQUENCE LISTING

```
<160> NUMBER OF SEQ ID NOS: 4

<210> SEQ ID NO 1
<211> LENGTH: 930
<212> TYPE: DNA
<213> ORGANISM: Streptomyces coelicolor A3(2)

<400> SEQUENCE: 1
gtggtcaacc gacgtgatct catcaagtgg agtgccgtcg cactcggagc gggtgcgggg      60
ctcgcgggtc ccgcacccgc cgctcatgcc gcagacctcg aatgggaaca gtaccccgtg     120
ccggccgccc ctggcggaaa caggtcctgg cagcttctcc ccagccattc ggacgacttc     180
aactacaccg gcaagcctca aaccttcagg ggcagatggc tggaccagca caaggatggc     240
tggtcgggcc cggccaacag cctctacagt gcgcgccatt cctgggtggc tgacggaaat     300
ctcatcgtcg agggccgcag ggcgccggac gggagggtct actgcggcta cgtgacctcc     360
cgcaccccag tcgagtaccc tctctatacc gaagtactca tgcgtgtgag cgggctgaag     420
ctctcatcga atttctggct cctgagcaga gacgacgtca acgagattga cgtgatcgaa     480
tgctacggca acgagtcatt gcacggaaag cacatgaaca ccgcctacca catattccag     540 cggaaccct tcactgaact ggcgagaagc cagaagcggt atttcgcaga tgggagctac     600
gggtacaatg gtgagactgg gcaggtgttt ggggacggcg ccgggcaacc tcttcttcgg     660
aatggattcc accgctacgg cgtgcactgg ataagcgcca ccgaattcga tttctacttc     720
aacggcaggt tggtgcgccg gctgaaccgg tcgaacgacc tcagggaccc ccggagccgg     780
ttcttcgacc agccaatgca tctgatcctc aacaccgaga gtcatcagtg gcgcgtcgac     840
cgaggtatcg aacccacgga cgcggaactc gcagaccccca gcatcaacaa catctactac     900
cgctgggtca ggacgtatca ggccgtgtag                                      930

<210> SEQ ID NO 2
```

```
<211> LENGTH: 309
<212> TYPE: PRT
<213> ORGANISM: Streptomyces coelicolor A3(2)

<400> SEQUENCE: 2
```

| Met | Val | Asn | Arg | Arg | Asp | Leu | Ile | Lys | Trp | Ser | Ala | Val | Ala | Leu | Gly |
|---|---|---|---|---|---|---|---|---|---|---|---|---|---|---|---|
| 1 | | | | 5 | | | | | 10 | | | | | 15 | |

Ala Gly Ala Gly Leu Ala Gly Pro Ala Pro Ala His Ala Ala Asp
           20             25             30

Leu Glu Trp Glu Gln Tyr Pro Val Pro Ala Ala Pro Gly Gly Asn Arg
      35             40            45

Ser Trp Gln Leu Leu Pro Ser His Ser Asp Asp Phe Asn Tyr Thr Gly
    50             55            60

Lys Pro Gln Thr Phe Arg Gly Arg Trp Leu Asp Gln His Lys Asp Gly
65              70            75             80

Trp Ser Gly Pro Ala Asn Ser Leu Tyr Ser Ala Arg His Ser Trp Val
          85             90            95

Ala Asp Gly Asn Leu Ile Val Glu Gly Arg Arg Ala Pro Asp Gly Arg
          100         105          110

Val Tyr Cys Gly Tyr Val Thr Ser Arg Thr Pro Val Glu Tyr Pro Leu
       115          120         125

Tyr Thr Glu Val Leu Met Arg Val Ser Gly Leu Lys Leu Ser Ser Asn
  130            135           140

Phe Trp Leu Leu Ser Arg Asp Asp Val Asn Glu Ile Asp Val Ile Glu
145            150           155          160

Cys Tyr Gly Asn Glu Ser Leu His Gly Lys His Met Asn Thr Ala Tyr
          165         170          175

His Ile Phe Gln Arg Asn Pro Phe Thr Glu Leu Ala Arg Ser Gln Lys
       180          185         190

Gly Tyr Phe Ala Asp Gly Ser Tyr Gly Tyr Asn Gly Glu Thr Gly Gln
  195            200           205

Val Phe Gly Asp Gly Ala Gly Gln Pro Leu Leu Arg Asn Gly Phe His
    210           215          220

Arg Tyr Gly Val His Trp Ile Ser Ala Thr Glu Phe Asp Phe Tyr Phe
225            230           235          240

Asn Gly Arg Leu Val Arg Arg Leu Asn Arg Ser Asn Asp Leu Arg Asp
          245         250          255

Pro Arg Ser Arg Phe Phe Asp Gln Pro Met His Leu Ile Leu Asn Thr
       260          265         270

Glu Ser His Gln Trp Arg Val Asp Arg Gly Ile Glu Pro Thr Asp Ala
  275            280           285

Glu Leu Ala Asp Pro Ser Ile Asn Asn Ile Tyr Tyr Arg Trp Val Arg
    290           295          300

Thr Tyr Gln Ala Val
305

```
<210> SEQ ID NO 3
<211> LENGTH: 27
<212> TYPE: DNA
<213> ORGANISM: Artificial Sequence
<220> FEATURE:
<223> OTHER INFORMATION: forward primer for cloning DagA(Asm-F)

<400> SEQUENCE: 3
gacatatggt ggtcaaccga cgtgatc                                          27
```

```
<210> SEQ ID NO 4
<211> LENGTH: 26
<212> TYPE: DNA
<213> ORGANISM: Artificial Sequence
<220> FEATURE:
<223> OTHER INFORMATION: reverse primer for cloning DagA(Asm-R)

<400> SEQUENCE: 4
ggtggatccc tacacggcct gatacg                                          26
```

COMPOSITION FOR PREVENTING, ALLEVIATING, OR TREATING ARTHRITIS OR OSTEOPOROSIS, CONTAINING NEOAGAROOLIGOSACCHARIDE

CROSS REFERENCE TO RELATED APPLICATIONS

This application is a National Stage of International Application No. PCT/KR2017/011436 filed Oct. 17, 2017, claiming priority based on Korean Patent Application No. 10-2016-0140731 filed Oct. 27, 2016.

TECHNICAL FIELD

The present invention relates to a composition for preventing, alleviating, or treating arthritis or osteoporosis, containing neoagarooligosaccharide, and the composition for preventing, alleviating, or treating arthritis or osteoporosis is characterized by effectively inhibiting the differentiation of monocytes into osteoclasts.

BACKGROUND ART

For a long time, agar has been a representative algae-derived polysaccharide widely used for food additives, medicines, cosmetics, livestock feed and industrial raw materials. In Korea, its annual production is about 2,000 tons to about 5,000 tons per year and thus agar is a relatively abundant fishery resource. Meanwhile, in actual use, only a portion of the total production amount is simple-processed to be used as cheap raw material, but the rest of the total amount is mostly neglected. Thus, its added value is very low compared to the amount of resources available. Thus, there is a high demand for researches on the development of new applications of agar abundant in Korea and the improvement of added value.

Agar is composed mostly of polysaccharides except for small amounts of protein, ash and fat. The polysaccharides constituting the agar include agarose, a neutral polysaccharide, and agaropectin, an acidic polysaccharide. Agarose includes a monomer of an agarobiose in which D-galactose and 3,6-anhydro-L-galactose are combined in a β-1,4 form, and Agarose has strong gelation strength because agarobiose has a straight-chain structure in which α-1,3 bonds are repeatedly connected to each other. On the other hand, agaropectin, like agarose, has agarobiose as a monomer but contains an acidic group such as a sulfate group and thus has a weak gelation strength.

Among them, agarose is digested into neoagarobiose via neoagarotetraose by β-agarase acting on β-1,4 bond, and then it is finally digested into D-galactose and 3,6-anhydro-L-galactose by α-agarase acting on α-1,3 bond. In addition, the agarose is digested to a neoagarobiose by dilute acid or α-agarase. In general, neoagarooligosaccharide means oligosaccharide having about 2 to 10 monosaccharides combined such as neoagarobiose, neoagarotetraose, neoagarohexaose and neoagarooctaose obtained by hydrolyzing agar or agarose with β-agarase. Further, agarooligosaccharide means oligosaccharide having about 2 to 10 monosaccharides combined such as agarobiose, agarotetraose, agarohexaose, and agarooctaose obtained by hydrolyzing agar or agarose with dilute acid or α-agarase. Neoagarooligosaccharide has 3,6-anhydro-L-galactose as a non-reducing end while agarooligosaccharide has D-galactose as a non-reducing end. Due to these structural differences, they may exhibit different properties in terms of physiological activity.

Meanwhile, *Streptomyces coelicolor* A3 (2), actinomycetes, is known to produce an extracellular protein form of agarase (which is secreted out of cells) that digests agar (Stanier et al., 1942, J. Bacteriol.; Hodgson and Chater, 1981, J. Gen. Microbiol.). The agarase is encoded by a DagA gene. The DagA gene is a 3-agarase gene whose function is the only known in actinomycetes and plays an important role in the studies on agarase production in actinomycetes. In particular, the *Streptomyces coelicolor* is the most widely used strain for the molecular biological study on actinomycetes, and the sequence of chromosomal DNA was analyzed and disclosed in the Sanger center in England in 2002 ((Bantley et al., 2002, Nature).

Regarding the preparation or use of neoagarooligosaccharide, Korean Patent No. 10-0794593 discloses a method for producing at least one neoagarooligosaccharide selected from the group consisting of neoagarobiose, neoagarotetraose and neoagarohexaose using *Thalassomonas* sp. strain, SL-5 KCCM 10790P, having an agar-digesting ability and a β-agarase produced by the strain. In addition, Korean Patent No. 10-1072503 discloses a method for producing at least one neoagarooligosaccharide selected from the group consisting of neoagarobiose, neoagarotetraose and neoagarohexaose using *Glaciecola* sp. strain, SL-12 KCCM 10945P, and a β-agarase produced by the strain. Further, Korean Patent No. 10-1303839 discloses a β-agarase isolated from *Pseudoalteromonas* sp strain and a method for producing at least one neoagarooligosaccharide selected from the group consisting of neoagarotetraose and neoagarohexaose using the β-agarase. Further, Korean Patent No. 10-1295659 discloses a β-agarase isolated from *Saccharophagus* sp. strain and a method for producing at least one neoagarooligosaccharide selected from the group consisting of neoagarotetraose and neoagarohexaose using the β-agarase. Further, Korean Patent No. 10-1212106 discloses a method for producing neoagarobiose by reacting a 3-agarase isolated from *Saccharophagus* sp. strain with at least one substrate from the group consisting of agar, neoagarotetraose and neoagarohexaose. Further, Korean Patent No. 10-1206006 discloses a method for producing at least one neoagarooligosaccharide selected from the group consisting of neoagarobiose, neoagarotetraose and neoagarohexaose by reacting agar with *Flammeovirga* sp. strain, mbrc-1 KCCM 11151P, and a β-agarase produced by the strain. Further, Korean Patent No. 10-1302655 discloses a method for producing neoagarotetraose and neoagarohexaose characterized by reacting agar or agarose with agarase derived from *Streptomyces coelicolor*. Further, Korean Patent No. 10-1190078 discloses a β-agarase recombinant expression vector including a DNA fragment represented by the nucleotide sequence represented by SEQ ID NO: 7 including a promoter of a trypsin gene (sprT) derived from *Streptomyces griseus* and a signal peptide coding region; and a DNA fragment represented by the nucleotide sequence represented by SEQ ID NO: 2 in which a signal peptide code has been removed from a β-agarase gene derived from *Streptomyces coelicolor* (dagA), which is capable of transforming prokaryotic cells and a method for producing β-agarase using the recombinant expression vector. Further, Korean Patent Laid-Open Publication No. 10-2014-0060045 discloses an enzymatic production method of neoagarobiose or neoagarotetraose using a novel β-agarase-producing gene. Further, Korean Patent Laid-Open No. 10-2009-0044987 discloses a skin whitening composition including neoagarotetraose as an active ingredient. As described above, the prior art has mainly focused on a novel strain including a β-agarase as a gene, a method for producing β-agarase by a novel strain or a recombinant strain, or a method for producing neoagarooligosaccharide from agar and the like using β-agarase. Therefore, the various physiological functions of neoagarooligosaccharides, especially neoagarooligosaccharides prepared using specific β-agarases, have been hardly studied in the prior art.

DISCLOSURE

Technical Problem

The present invention has been made under the conventional technical background, and an object of the present invention is to provide a novel food or pharmaceutical use of neoagarooligosaccharide.

Technical Solution

In order to archive the objects, an embodiment of the present invention provides a composition including a neoagarooligosaccharide mixture as an active ingredient, in which the neoagarooligosaccharide mixture includes neoagarobiose, neoagarotetraose, and neoagarohexaose, and in which the composition has use for preventing, alleviating, or treating arthritis or osteoporosis which is caused or progressed by the differentiation of mononuclear cells into osteoclasts.

In order to archive the objects, another embodiment of the present invention provides a composition including an enzyme reaction product of a substrate selected from agar or agarose with DagA as a beta-agarase derived from *Streptomyces coelicolor* or a purified product thereof as an active ingredient, in which the enzyme reaction product or the purified product thereof includes neoagarobiose, neoagarotetraose, and neoagarohexaose, and in which the composition has use for preventing, alleviating, or treating arthritis or osteoporosis which is caused or progressed by the differentiation of mononuclear cells into osteoclasts.

Advantageous Effects

The neoagarooligosaccharide mixture and the like as an active ingredient of the composition according to the present invention can reduce the expression of RANKL, which is an osteoclast inducer and effectively inhibit differentiation of monocytes into osteoclasts. Thus, the composition according to the present invention may be used as a medicine or functional food for preventing, alleviating, or treating arthritis (especially rheumatoid arthritis) or osteoporosis. Further, the active ingredient of the composition according to the present invention can be obtained by an enzyme reaction between a readily available substrate such as agar or agarose and DagA as a beta-agarase derived from *Streptomyces coelicolor*. Thus, it can be produced at a relatively low cost and can easily be ingested by anyone because it has no side effects.

DETAILED DESCRIPTION OF EMBODIMENT

Figure 1:
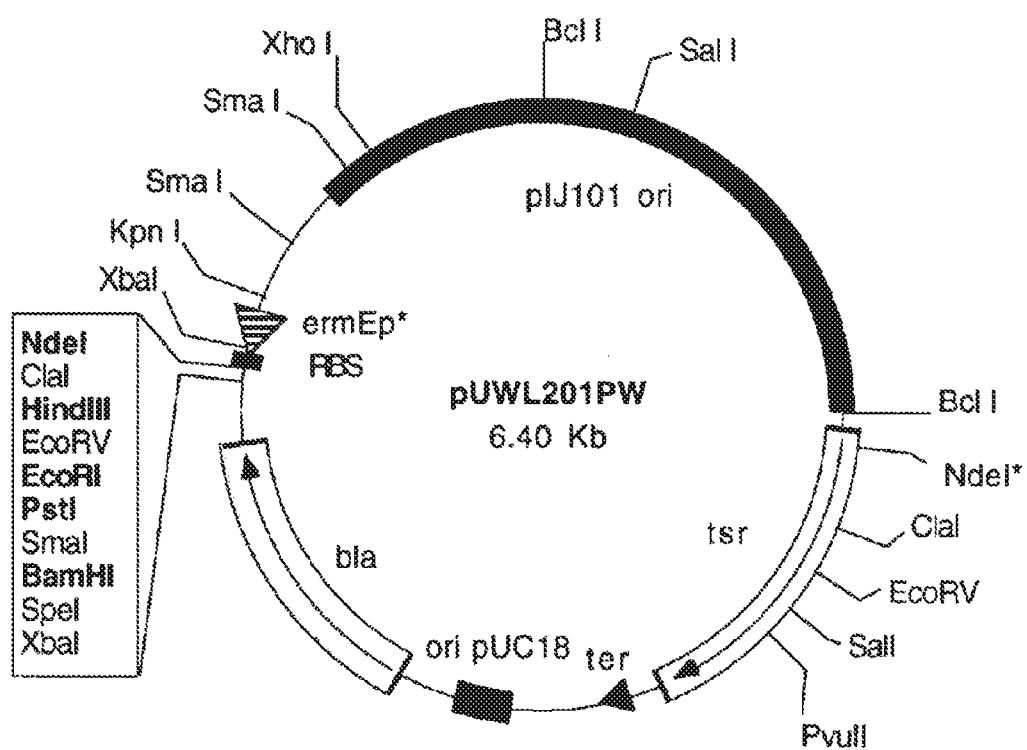
FIG. 1 is a cleavage map of the pUWL201pw vector used for cloning the DagA gene in the present invention.

Hereinafter, terms as used herein will be described.

As used herein, the terms "pharmaceutically acceptable" and "sitologically acceptable" refer to not significantly irritating the organism and not interfering with the biological activity and properties of the administered active substance.

As used herein, the term "prevention" means any action that inhibits the symptoms of a particular disease or slows the progression of the disease by administration of the composition of the present invention.

As used herein, the term "improvement" means any action that at least reduces the parameter associated with the condition being treated, for example, the degree of the symptom.

As used herein, the term "treatment" means any action that improves or alleviates the symptoms of a particular disease by administration of the composition of the present invention.

As used herein, the term "administration" is meant to provide any desired composition of the invention to an individual by any suitable method. In this regard, the individual means any animal such as a human, a monkey, a dog, a goat, a pig, or a mouse having a disease in which symptoms of a specific disease can be improved by administering the composition of the present invention.

As used herein, the term "pharmaceutically effective amount" means an amount sufficient to treat a disease at a reasonable benefit or risk rate applicable to medical treatment, and it can be determined depending on factors including the disease type, severity, the drug activity, the sensitivity to drugs, the administration time, the administration route, the drug excretion rate, the treatment duration, drugs used simultaneously and other factors well known in the medical arts.

Hereinafter, the present invention will be described in detail.

The composition for preventing, improving or treating arthritis or osteoporosis according to an embodiment of the present invention includes a neoagarooligosaccharide mixture as an active ingredient. The neoagarooligosaccharide mixture includes neoagarobiose, neoagarotetraose and neoagarohexaose. The neoagarooligosaccharide mixture preferably includes 1% by weight to 10% by weight of neoagarobiose, 55% by weight to 75% by weight of neoagarotetraose and 20% by weight to 40% by weight of neoagarohexaose with respect to the total weight of the neoagarooligosaccharide mixture and more preferably includes 2% by weight to 4% by weight of neoagarobiose, 65% by weight to 70% by weight of neoagarotetraose and 25% by weight to 30% by weight of neoagarohexaose with respect to the total weight of the neoagarooligosaccharide mixture, considering the synergistic effects of the constituents. Further, the neoagarooligosaccharide mixture may be an enzyme reaction product of a substrate selected from agar or agarose with DagA, a beta-agarase derived from *Streptomyces coelicolor*, or a purified product thereof. A method for obtaining a neoagarooligosaccharide mixture through an enzyme reaction between a substrate and DagA will be described in detail as below.

The composition for preventing, improving or treating arthritis or osteoporosis according to another embodiment of the present invention includes an enzyme reaction product of a substrate selected from agar or agarose with DagA, a beta-agarase derived from *Streptomyces coelicolor*, or a purified product thereof as an active ingredient. The enzyme reaction product or purified product thereof includes neoagarobiose, neoagarotetraose and neoagarohexaose. Further, the enzyme reaction product or purified product thereof preferably includes 1% by weight to 10% by weight of neoagarobiose, 55% by weight to 75% by weight of neoagarotetraose and 20% by weight to 40% by weight of neoagarohexaose with respect to the total weight of the neoagarooligosaccharide and more preferably includes 2% by weight to 4% by weight of neoagarobiose, 65% by weight to 70% by weight of neoagarotetraose and 25% by weight to 30% by weight of neoagarohexaose with respect to the total weight of the neoagarooligosaccharide. Further, the enzyme reaction is preferably carried out at a temperature of 35° C. to 45° C. and a pH of 6 to 8. In addition, the enzyme reaction may be carried out by adding DagA having a concentration of 2 unit/ml to 250 unit/ml, preferably 10 unit/ml to 150 unit/ml, more preferably 10 unit/ml to 100 unit/ml to 0.5 to 5% (w/v) agar or agarose solution. In this regard, one unit representing enzyme activity is defined as the amount of enzyme as described below. 3.9 ml of a 50 mM PBS solution (pH 7) in which the agarose is dissolved at a concentration of 0.2% (w/v) is reacted at 40° C. for 5 minutes (4 ml of the reaction solution), and DNS reagent (6.5 g of dinitrosalicylic acid, 325 ml of 2 M NaOH and 45 mL of glycerol are dissolved in 1 liter of distilled water) having the same amount of the reaction solution is added. The mixture is boiled for 10 minutes and is cooled. Thus, one unit is defined as the amount of enzyme that shows absorbance of 0.001 at 540 nm when the mixture's absorbance is measured at 540 nm.

Hereinafter, a method for obtaining active ingredients of the composition according to the present invention through the enzyme reaction between the substrate and DagA will be described. In the present invention, DagA derived from *Streptomyces coelicolor* means a protein having an amino acid sequence between 31 and 309 represented by SEQ ID NO: 2 and includes proteins produced from *Streptomyces coelicolor* or heterologous strains or all proteins recombined according to methods such as the conventional gene recombinant methods within the scope that the function is not changed to a totally different function, or that the agarase activity is not lost, in other words, a method of incorporating a labeling amino acid for the favorable purification or altering amino sequences for heterologous expression. When DagA is translated initially from the beta-agarase gene of *Streptomyces coelicolor*, it has 309 amino acids represented by SEQ ID NO: 2 and is produced with a molecular weight of about 35 kDa. DagA is secreted in the form of the completed extracellular protein (about 32 kDa) with the cleavage of 30 amino acid signal peptides at the N-terminal thereof. The DagA gene of *Streptomyces coelicolor* can be represented by the nucleotide sequence represented by SEQ ID NO: 1. SEQ ID NO: 1 is the nucleotide sequence of the gene present in the genome of *Streptomyces coelicolor* A3 (2) and is named "SCO3471" on NCBI (US National Bioinformation Center) database. As confirmed by in vitro experiments, the transcription of the DagA gene is regulated by four or five different promoters that are recognized by at least three different holoenzymes of the RNA polymerase. Transcription step analysis of the DagA gene indicated that the transcription of DagA was initiated at the upper parts, 32nd, 77th, 125th and 220th bases of the coding sequence.

Although DagA used in the present invention can be produced by the cultivation of *Streptomyces coelicolor*, which is a production strain of DagA, it is preferable to use an expression system of *Streptomyces lividans*, which is a heterologous strain, in order to increase production efficiency. DagA can be produced by a method in which the DagA gene is inserted into an actinomycete vector to prepare a recombinant vector, then *Streptomyces lividans* is transformed with a recombinant vector, and then the transformant is cultured. In this case, the recombinant vector is preferably constructed such that the transcription of the DagA gene can be regulated by the actinomycete-derived promoter. The actinomycete-derived promoter includes various promoters such as sgtR promoter (sgtRp), ermE promoter (ermEp), and tipA promoter (tipAp). Thus, these may be selected and used when preparing recombinant vectors. Several kinds of vectors have been developed to be constructed so that transcription can be regulated by these promoters. When SCO3471 is cloned into these vectors, a recombinant vector having a structure in which transcription is regulated by actinomycetes-derived promoter can be produced. The transformant can be prepared by transforming the host strain with the DagA gene-cloned recombinant vector. Since transformation methods vary depending on the host strain, an appropriate method may be selected and used. For example, when *Streptomyces lividans* is used as a host strain, a transformation method using polyethylene glycol (PEG) as a mediator may be used. A DagA producing strain such as a transformant may be cultured in a liquid medium to produce DagA. The culture solution is obtained, and a conventional protein purification method such as an ultrafiltration method is used so that a high purity DagA may be produced. At this time, if agar or agarose is included in the liquid medium, DagA may be produced more efficiently.

The DagA thus produced is added to a substrate solution such as agar or agarose, and the mixture is reacted at a specific temperature and pH, thereby obtaining an enzyme reaction product which is used as an active ingredient in the composition according to the present invention. Further, the enzyme reaction product can be partially purified by ultrafiltration or passed through the gel filtration chromatography to be fractionated, thereby obtaining a purified product of the enzyme reaction product.

The neoagarooligosaccharide mixture and the like, which are an active ingredient of the composition according to the present invention, reduces the expression of RANKL, an osteoclast inducer, or IL-6, an inflammatory cytokine, and effectively inhibits the differentiation of mononuclear cells into osteoclasts. An osteoclast is a multinuclear giant cell having functions of destruction and absorption of bone tissue and is known to be involved in arthritis or osteoporosis. The bone tissue is a dynamic organ which is maintained by repeating osteoblast-induced osteogenesis and osteoclast-induced bone resorption. As the differentiation of mononuclear cells into osteoclasts increases, the bone absorption is more than the bone generation so that arthritis (particularly rheumatoid arthritis) or osteoporosis occurs or progresses. For this reason, studies on the development for the treatment of arthritis (particularly rheumatoid arthritis) or osteoporosis focus on the search for materials that inhibit osteoclast formation or inhibit osteoclast activation. Therefore, the neoagarooligosaccharide mixture, which is an active ingredient of the composition according to the present invention, can be used as a substance for preventing, ameliorating or treating arthritis (particularly rheumatoid arthritis) or osteoporosis. The composition according to the present invention may be formulated into a pharmaceutical composition, a food additive, a food composition (particularly a functional food) or a feed additive depending on the intended use or aspect, and the content of the active ingredient included in the composition may also be adjusted in various ranges depending on its specific form, purposes or aspects.

When the composition for preventing, ameliorating or treating arthritis or osteoporosis according to the present invention is formulated into a pharmaceutical composition, the content of the active ingredient in the pharmaceutical composition is not particularly limited and may be, for example, 0.1% by weight to 99% by weight, preferably 0.5% by weight to 50% by weight, more preferably 1 by weight to 30% by weight. In addition, the pharmaceutical composition of the present invention may further contain an additive such as a pharmaceutically acceptable carrier, excipient or diluent in addition to the active ingredient. Examples of carriers, excipients and diluents that can be included in the pharmaceutical composition of the present invention include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. In addition, the pharmaceutical composition of the present invention may contain at least one known active ingredient having effects of preventing, improving or treating arthritis or osteoporosis in addition to neoagarooligosaccharide. The pharmaceutical composition of the present invention can be formulated into a formulation for oral administration or parenteral administration by a conventional method and can be formulated using a diluent or an excipient such as a filler, an extender, a binder, a wetting agent, a disintegrant and a surfactant commonly used in the formulation. Examples of solid formulations for oral administration may include a tablet, a pill, a powder, a granule, and a capsule. Such solid formulations may be prepared by mixing the combined extract, an active ingredient, with at least one excipient, e.g., starch, calcium carbonate, sucrose, lactose, or gelatin. Also, a lubricant such as magnesium stearate or talc may be used in addition to a simple excipient. Examples of the liquids for oral administration include a suspension, an internal solution, an emulsion, and a syrup, and the liquids may further include various types of excipient including a wetting agent, a sweetener, a flavoring agent and a preservative, in addition to a simple diluent such as water or liquid paraffin. Examples of formulations for parenteral administration may include a sterilized aqueous solution, a non-aqueous solvent, a suspension, an emulsion, a lyophilized preparation, and a suppository. Examples of the non-aqueous solvents and the suspensions include propylene glycol, polyethylene glycol, vegetable oil including olive oil, and injectable esters including ethyl oleate. Bases for the suppositories may be witepsol, macrogol, tween 61, cacao butter, Laurin, or glycerogelatin. Further, the composition may be desirably formulated according to diseases or ingredients using a proper method known in the related art, or a method disclosed in Remington's Pharmaceutical Science (the latest version), Mack Publishing Company, Easton Pa. The pharmaceutical composition of the present invention may be administered orally or parenterally to a mammal including a human according to a desired method. The parenteral administration method includes dermal application, intraperitoneal injection, intrarectal injection, subcutaneous injection, intravenous injection, intramuscular injection or intrathoracic injection. The dose of the pharmaceutical composition of the present invention is not limited as long as it is a pharmaceutically effective amount, and it varies depending on the body weight, age, sex, and health condition of a patient, diet, an administration time, an administration method, a release rate, and severity of a disease. The typical daily dose of the pharmaceutical composition of the present invention is not particularly limited, for example, preferably 0.1 mg/kg to 1000 mg/kg, more preferably 1 mg/kg to 500 mg/kg based on the combined extract as an active ingredient. Further, the composition may be administered once a day, or administered in divided doses.

Further, when the composition for preventing, ameliorating or treating arthritis or osteoporosis according to the present invention is formulated into a food composition, the content of the active ingredient in the food composition is not particularly limited and may be 0.01% by weight to 50% by weight, preferably 0.1% by weight to 25% by weight, and more preferably 0.5% by weight to 10% by weight with respect to the total weight of the composition. The food composition of the present invention may be in the form of a pill, a powder, a granule, an infusion, a tablet, a capsule, or a liquid preparation. Examples of the food include meat, sausage, bread, chocolate, candy, snack, confectionery, pizza, ramen, other noodles, gum, dairy products including ice cream, various soups, beverage, tea, functional water, drink, alcoholic beverage and vitamin complex, and include all health food in the usual meaning. The food composition of the present invention may contain various flavors or natural carbohydrates as an additional ingredient in addition to the active ingredient. In addition, the food composition of the present invention may include various nutrients, a vitamin, an electrolyte, a flavor, a colorant, pectic acid and its salts, alginic acid and its salts, organic acid, a protective colloid thickener, a pH adjuster, a stabilizer, a preservative, glycerin, alcohol, a carbonating agent used in carbonated drinks and the like. Further, the food composition of the present invention may contain natural fruit juices and flesh for the production of fruit juice drinks and vegetable drinks. These ingredients may be used independently or in combination. The above-mentioned natural carbohydrates are monosaccharides such as glucose and fructose, disaccharides such as maltose and sucrose, polysaccharides such as dextrin and cyclodextrin, and sugar alcohols such as xylitol, sorbitol and erythritol. Natural flavors such as thaumatin and stevia extract and synthetic flavors such as saccharin and aspartame may be used as the flavor.

Another example of the present invention provides a method for preventing, improving or treating arthritis or osteoporosis by administering an effective amount of a neoagarooligosaccharide mixture to an individual in need thereof. Further, the present invention provides a method for preventing, improving or treating arthritis or osteoporosis by administering an effective amount of a composition including a neoagarooligosaccharide mixture to an individual in need thereof. Further, the present invention provides a method for preventing, improving or treating arthritis or osteoporosis by administering an effective amount of an enzyme reaction product between a substrate selected from agar or agarose and DagA, a beta-agarase derived from *Streptomyces coelicolor* or a purified product thereof to an individual in need thereof. Further, the present invention provides a method for preventing, improving or treating arthritis or osteoporosis by administering an effective amount of the composition including an enzyme reaction product between a substrate selected from agar or agarose and DagA, a beta-agarase derived from *Streptomyces coelicolor* or a purified product thereof to an individual in need thereof.

Hereinafter, the present invention will be described in more detail with reference to Examples. However, the following Examples are intended to clearly illustrate the technical features of the present invention and do not limit the scope of protection of the present invention.

Example 1: Production of DagA Enzyme

Polymerase chain reaction (PCR) was performed using the chromosomal DNA of *Streptomyces coelicolor* A3 (2) as a template and using the following primer and Ex-Taq (TAKARA) polymerase. As a result, the amplified DagA gene fragment (a fragment of 947 bp in length encoded with the signal peptide of DagA and completed peptide, corresponding to a part of the sequence of the primer connected to both terminals of the nucleotide sequence represented by SEQ ID NO: 1) was obtained.

Primers used for amplification of the DagA gene fragment

```
Asm-F (Forward Primer):
(NdeI)
                                           (SEQ ID NO: 3)
5'-GACATATGGTGGTCAACCGACGTGATC-3'

Asm-R (Reverse Primer):
(BamHI)
                                           (SEQ ID NO: 4)
5'-GGTGGATCCCTACACGGCCTGATACG-3'
```

Figure 2:
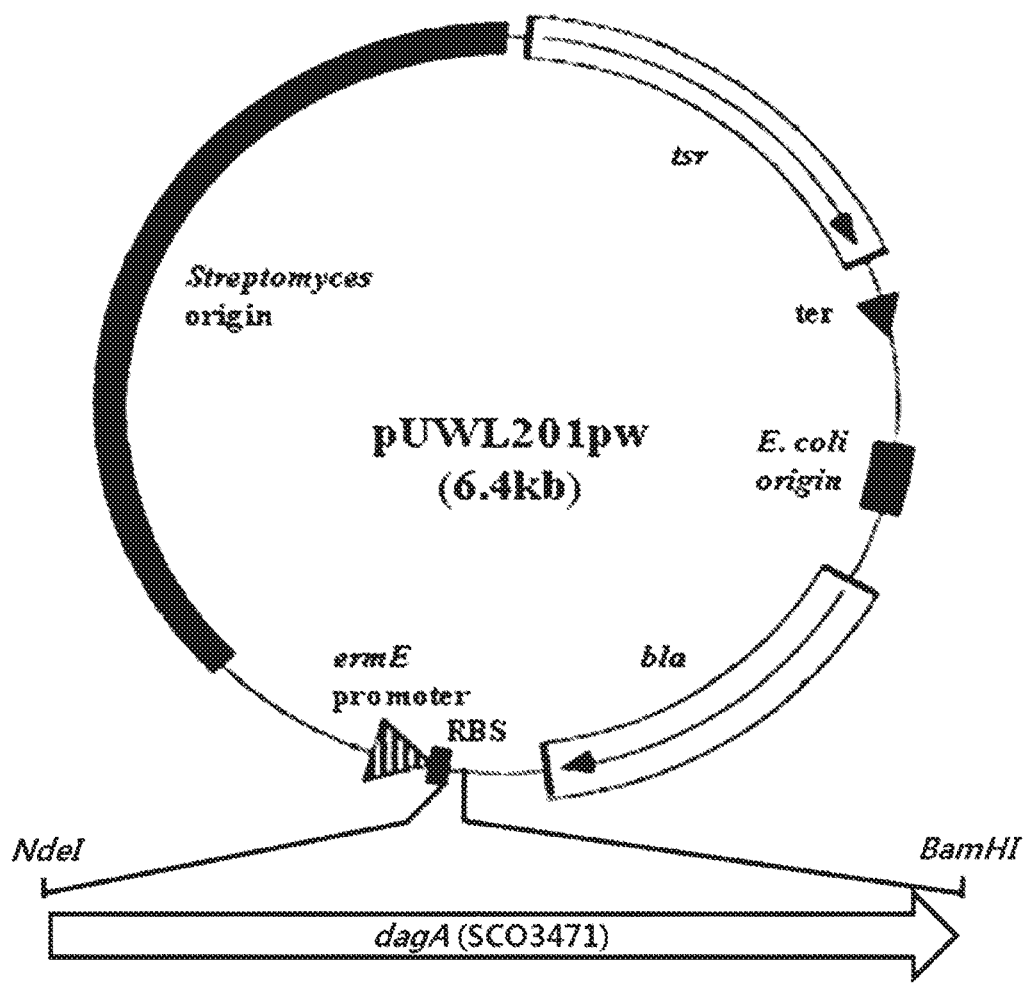
FIG. 2 is a cleavage map of a recombinant vector into which the DagA gene is introduced into the pUWL201pw vector.

Then, the DagA gene was cloned into the pUWL201pw vector shown in FIG. 1 using the restriction enzyme site (NdeI/BamHI) of the amplified DagA gene fragment to prepare the recombinant vector shown in FIG. 2. In the recombinant vector shown in FIG. 2, transcription of the DagA gene was regulated by the ermE promoter. Then, *Streptomyces lividans* TK24 strain was transformed with the recombinant vector shown in FIG. 2 to prepare a recombinant strain, and the recombinant strain was used for the production of DagA.

Specifically, the recombinant strain was inoculated into an R2YE liquid medium containing 0.3% (w/v) agar and pre-cultured for about 60 hours at 28° C. and a stirring condition of 120 rpm. After the pre-culture, the present culture was carried out for about 60 hours. The culture solution obtained through the present culture was centrifuged to remove microbial cells, and the supernatant was separated and purified by filtration through an ultrafiltration membrane (5 kDa cut-off membrane). The enzyme concentrate which did not pass through the filtration membrane was freeze-dried to be solidified, and the solidified DagA enzyme was stored and used in the subsequent experiments.

Example 2: Measurement of Agarase Activity of DagA Enzyme

The agarase activity of the DagA enzyme obtained in Example 1 was measured by the method of quantitating reducing sugar (e.g., DNS method). 100 µl of the DagA enzyme solution prepared by dissolving the DagA enzyme obtained in Example 1 in phosphate buffered saline (PBS) at a concentration of 10 mg/ml and 3.9 ml of 50 mM PBS solution (pH 7) in which the agarose was dissolved at a concentration of 0.2% (w/v) were mixed and reacted at 40° C. for 5 minutes. Then, 4 ml of DNS reagent (prepared by dissolving 6.5 g of dinitrosalicylic acid, 325 ml of 2M NaOH and 45 ml of glycerol in 1 liter of distilled water) was added thereto. The mixture was boiled for 10 minutes, then cooled, and the absorbance was measured at 540 nm. 1 U (Unit) of the enzyme is defined as an activity with an absorbance of 0.001 at 540 nm.

Example 3: Preparation of DagA Enzyme Reaction Products

1 L of a 20 mM Tris-HCl solution in which agar was dissolved at a concentration of 1.5% (w/v) was prepared, heated at 100° C. for about 10 minutes, and then cooled to 40° C. 125 U/ml DagA enzyme solution was added so as to be 20,000 U based on the amount of the whole sample, and the mixture was reacted for about 24 hours. Then, the enzyme reaction product was centrifuged to remove the undegraded agar, the supernatant was collected, and the enzyme reaction product was confirmed by the thin layer chromatography (TLC). The collected supernatant was partially purified by filtration through an ultrafiltration membrane (5 KDa cut-off membrane). The DagA enzyme reaction product passed through the filter membrane was lyophilized to be solidified. The solidified DagA enzyme reaction product was stored and used in the subsequent experiments. The above procedure was repeated to obtain partially purified enzyme reaction products corresponding to four batches.

Example 4: Identification of Neoagarooligosaccharide Composition of DagA Enzyme Reaction Product by HPLC-ELSD Analysis The neoagarooligosaccharide composition of the enzyme reaction product obtained in Example 3 above was identified by HPLC-ELSD analysis. HPLC-ELSD analysis conditions are as follows.

Column: $NH_2$ P-50 4E multimode column (250 mm×4.6 mm)

Mobile phase: a mixed solution of acetonitrile and water (acetonitrile and water in a volume ratio of 65:35)

Figure 3:
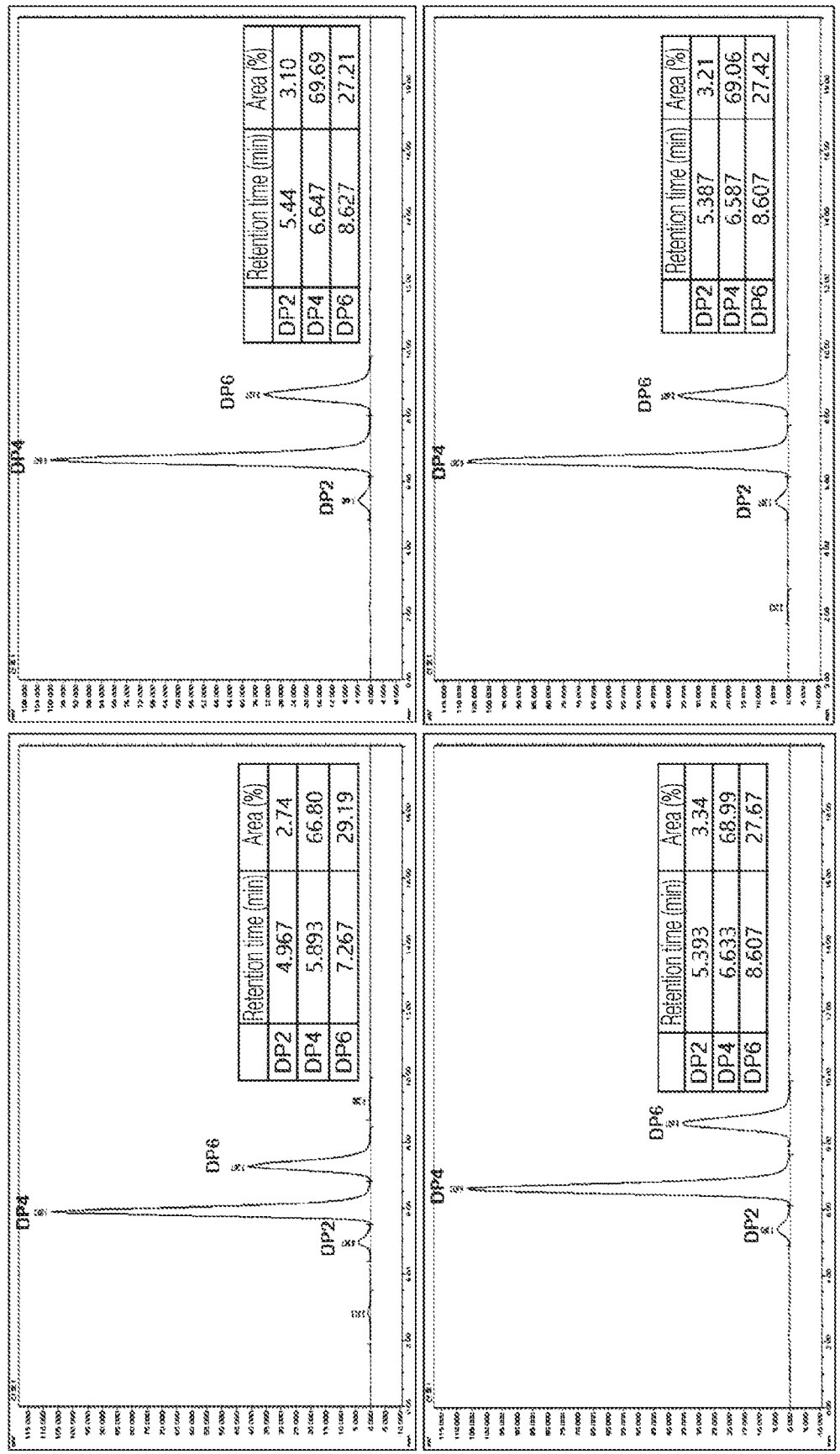
FIG. 3 is a graph showing the results of HPLC-ELSD analysis of the partially purified DagA enzyme reaction product obtained in Example 3 of the present invention.

FIG. 3 is a graph showing the results of HPLC-ELSD analysis of the partially purified DagA enzyme reaction product obtained in Example 3. The four peak graphs shown in FIG. 3 correspond to the partially purified enzyme reaction products obtained in the four batches, respectively. In addition, the area (%) shown in the table in FIG. 3 represents a percentage of the area of the peak corresponding to each neoagarooligosaccharide to the total peak area and can be interpreted in the same meaning as % by weight in the art. As shown in FIG. 3, the DagA enzymatic reaction products are mainly composed of neoagarooligosaccharide such as neoagarobiose (hereinafter referred to as "DP2"), neoagarotetraose (hereinafter referred to as "DP4"), and neoagarohexaose, (hereinafter referred to as "DP6"). The content of neoagarooligosaccharide in the DagA enzyme reaction product was found to be about 65±5% by weight with respect to the total weight of solids (including components not detected in HPLC-ELSD analysis). Further, the content can be selected from a wide range depending on the enzyme reaction conditions. For example, the content of neoagarooligosaccharide in the DagA enzyme reaction product may be 65±20% by weight with respect to the total weight of solids. Also, the content of DP2, DP4 and DP6, respectively, in the DagA enzyme reaction product was 2% by weight to 4% by weight, 65% by weight to 70% by weight and 25% by weight to 30% by weight with respect to the total weight of neoagarooligosaccharide combined with DP2, DP4 and DP6. However, the above content can be selected in various ranges depending on the enzyme reaction conditions. For example, the contents of DP2, DP4 and DP6, respectively, in the DagA enzyme reaction product may be 1% by weight to 10% by weight, 55% by weight to 75% by weight and 20% by weight to 40% by weight with respect to the total weight of neoagarooligosaccharide combined with DP2, DP4 and DP6.

Example 5: Purification of DagA Enzyme Reaction Products Using Gel Filtration Chromatography The partially purified enzyme reaction product obtained in Example 3 was separated and purified by gel permeation chromatography (GPC; BioGel P-2 gel, Biorad, Cat. No. 150-4115) to obtain neoagarohexaose (DP6), neoagarotetraose (DP4) and neoagarobiose (DP2). The purified products were then lyophilized to be solidified, and the solidified DagA enzyme reaction purified product was stored and used in subsequent experiments. The purity of the purified products including DP2, DP4 and DP6, was found to be about 85% (w/w) by TLC and HPLC.

Example 6: Test for Confirming the Efficacy of Neoagarooligosaccharide Mixture for Improving Rheumatoid Arthritis and Osteoporosis 6-1. Experimental Method (1) Cultivation of Synovial Cells (Fibroblasts-Like Synoviocytes) in Patients with Rheumatoid Arthritis During the arthroplasty of rheumatoid arthritis patients, arthritic tissue was isolated and treated with collagenase to isolate synovial cells. The synovial cells isolated from patients with rheumatoid arthritis were cultured in DMEM (Dulbecco's Modified Eagle's Medium) containing 10% FBS (Fetal Bovine Serum) at a concentration of 10% by weight. In this experiment, cells with a passage of 5 to 10 were used. The cells were seeded in a 6-well plate at an amount of $3\times10^5$ per well and stimulated with IL-17, an inflammatory cytokine. In order to examine the effect of the neoagarooligosaccharide mixture, synovial cells were pre-treated with partially purified DagA enzyme reaction products obtained in Example 3 (hereinafter referred to as 'NAO').

(2) Isolation of human peripheral blood mononuclear cells and induction of differentiation of human peripheral blood mononuclear cells into osteoclasts A blood buffer solution was prepared by mixing blood with PBS (Phosphate-Buffered Saline) solution at a volume ratio of 1:1. Then, ficoll was slowly floated on the tube containing the blood buffer solution while the ficoll layer was not disturbed (the weight ratio of the ficoll to the blood buffer was 1:4). The mixture was centrifugated at 2000 rpm for 30 minutes to collect only buffy coat layer. Then, the collected buffy coat layer was placed into a new tube and washed with PBS to obtain peripheral blood mononuclear cells (PBMC). Then, peripheral blood mononuclear cells (PBMC) were seeded and cultured into a 48-well plate in an amount of $5\times10^5$ per well. In order to induce the differentiation of peripheral blood mononuclear cells into osteoclasts, M-CSF and IL-17 stimulation were given. In order to examine inhibitory effect of the neoagarooligosaccharide mixture on the differentiation, peripheral blood mononuclear cells were pre-treated with the partially purified DagA enzyme reaction product obtained in Example 3 (hereinafter referred to as "NAO").

(3) Real-Time PCR

Levels of specific gene expression were analyzed by real-time PCR. Primers for specific genes used in PCR are shown in Table 1 below.

TABLE 1

| Gene type | Forward primer base sequence | Reverse primer base sequence |
|---|---|---|
| RANKL | ACC AGC ATC AAA ATC CCA AG | CCC CAA AGT ATG TTG CAT CC |
| IL-6 | CCC ACA CAG ACA GCC ACT CA | GGT TGT TTT CTG CCA CTG CC |
| β-actin | GAA ATC GTG CGT GAC ATC AAA G | TGT AGT TTC ATG GAT GCC ACA |
| TRAP | GAC CAC CTT GGC AAT GTC TCT G | TGG CTG AGG AAG TCA TCT GAG TTG |
| Cathepsin K | TGA GGC TTC TCT TGG TGT CCA TAC | AAA GGG TGT CAT TAC TGC GGG |
| calcitonin receptor | TGG TGC CAA CCA CTA TCC ATG C | CAC AAG TGC CGC CAT GAC AG |

Further, during real-time PCR analysis, nucleic acid was labeled using SYBR Green I (Roche Diagnostic, Mannheim, Germany) and fluorescence intensity was measured using a light cycler instrument (Roche Diagnostic).

(4) TRAP (Tartrate-Resistant Acid Phosphatase) Staining

Cells were placed in each well of a 48-well plate, and 1 ml of formaldehyde was added to each well for cell fixation and then maintained at room temperature for 10 minutes. Then, the fixative was suctioned, and the cells were washed three times with distilled water. Then, TRAP stain solution (Sigma, USA) was added to each well, and the mixture was reacted at 37° C. for 30 minutes. Then, the distilled water was added to each well, and the suction process was repeated three times, and then the cells were measured by a microscope.

Figure 4:
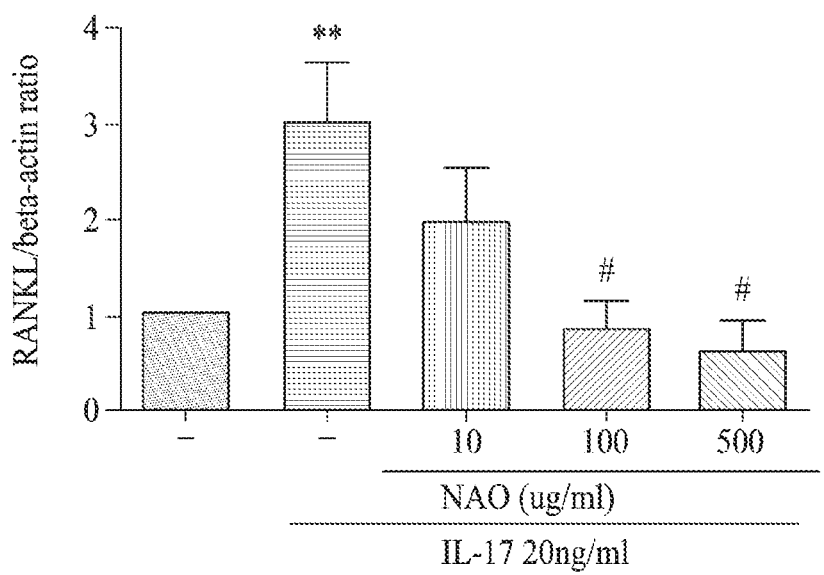
FIG. 4 shows the effect of neoagarooligosaccharide mixture (NAO) on the expression of RANKL (Receptor activator of nuclear factor kappa-B ligand), which is an osteoclast inducer, in synovial cells of patients with rheumatoid arthritis.

6-2. Experiment Result (1) Inhibitory Effect of Neoagarooligosaccharide Mixture on Osteoclastinducer in Synovial Cells of Patients with Rheumatoid Arthritis FIG. 4 shows the effect of neoagarooligosaccharide mixture (NAO) on the expression of RANKL (Receptor activator of nuclear factor kappa-B ligand), an osteoclast inducer, in synovial cells of patients with rheumatoid arthritis. As shown in FIG. 4, when IL-17, which is an inflammatory cytokine, was treated on synovial cells of patients with rheumatoid arthritis, the activity of RANKL, which is an osteoclast inducer, was increased. However, when neoagarooligosaccharide mixture (partially purified DagA enzyme reaction products obtained in Example 3, NAO) was treated thereon, the expression of RANKL was decreased in a concentration-dependent manner.

Figure 5:
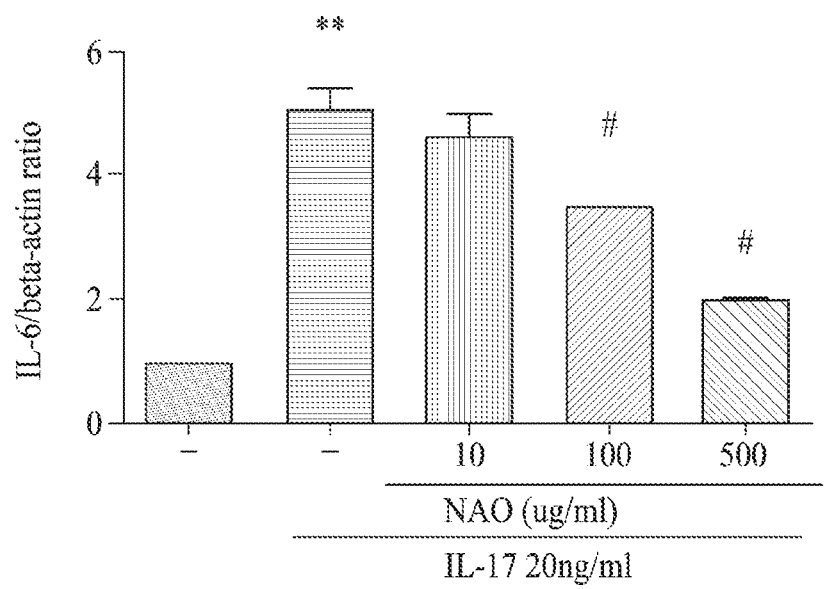
FIG. 5 shows the effect of neoagarooligosaccharide mixture (NAO) on the expression of IL-6, which is an inflammatory cytokine, in synovial cells of patients with rheumatoid arthritis.

(2) Inhibitory Effect of Neoagarooligosaccharide Mixture on IL-6 in Synovial Cells of Patients with Rheumatoid Arthritis FIG. 5 shows the effect of neoagarooligosaccharide mixture (NAO) on the expression of IL-6, an inflammatory cytokine, in synovial cells of patients with rheumatoid arthritis. As shown in FIG. 5, when IL-17, which is an inflammatory cytokine, was treated on synovial cells of patients with rheumatoid arthritis, the activity of IL-6, an inflammatory cytokine, was increased. However, when neoagarooligosaccharide mixture (partially purified DagA enzyme reaction products obtained in Example 3, NAO) was treated thereon, the expression of IL-6 was decreased in a concentration-dependent manner.

Figure 6:
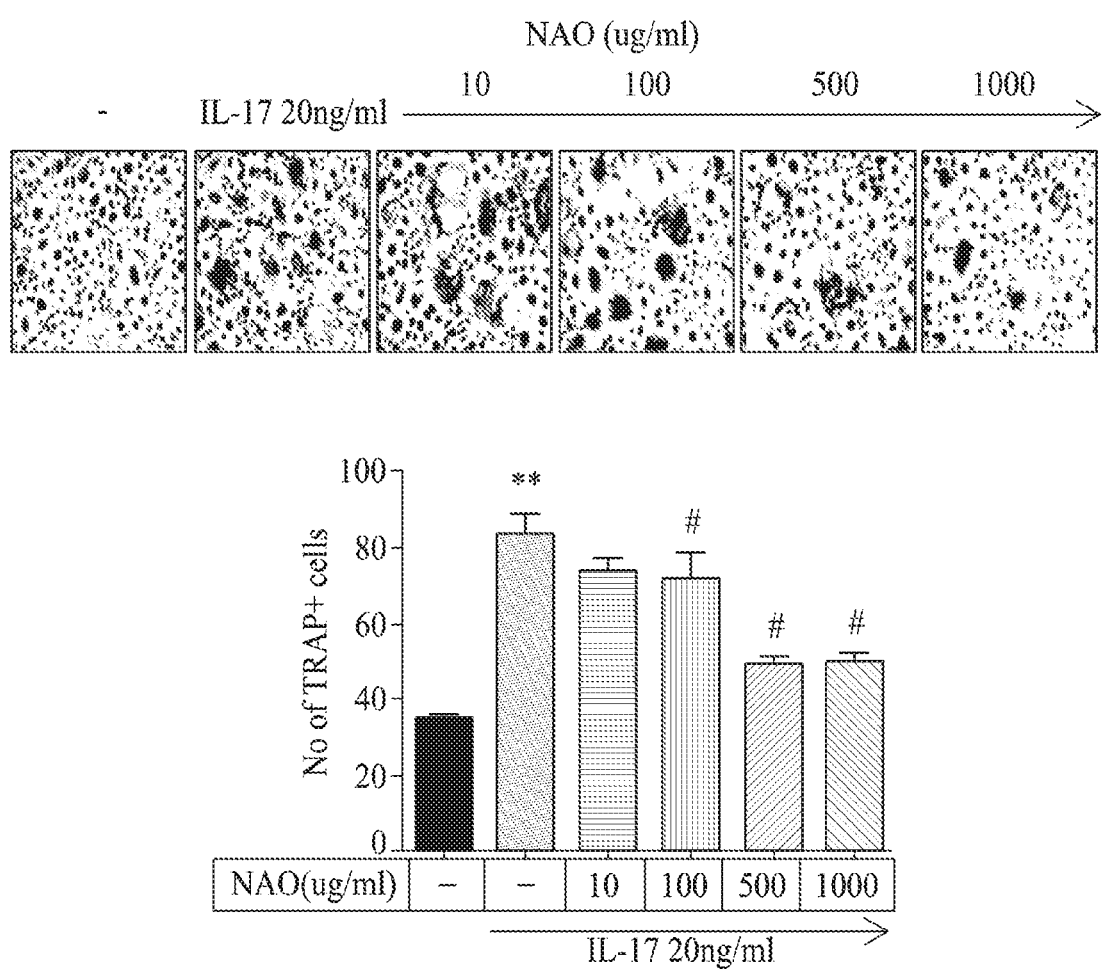
FIG. 6 shows the effect of neoagarooligosaccharide mixture (NAO) on osteoclast differentiation under the condition of inducing differentiation of peripheral blood mononuclear cells into osteoclasts.

(3) Inhibitory Effect of Neoagarooligosaccharide Mixture on the Differentiation into Osteoclasts Under Differentiation Induction Conditions of Peripheral Blood Mononuclear Cells into Osteoclasts Human peripheral blood mononuclear cells were isolated and stimulated with IL-17, an inflammatory cytokine, to induce differentiation into osteoclasts. Tartrate-resistant acid phosphatase (TRAP) staining was performed on the pretreated group and the untreated control group with the neoagarooligosaccharide mixture. FIG. 6 shows the effect of neoagarooligosaccharide mixture (NAO) on the differentiation into osteoclasts under the differentiation induction condition of peripheral blood mononuclear cells to osteoclast.

As shown in FIG. 6, when the neoagarooligosaccharide mixture (the partially purified DagA enzyme reaction product obtained in Example 3, NAO) was pretreated at a high concentration in human peripheral blood mononuclear cells, the differentiation into osteoclasts was remarkably suppressed.

Figure 7:
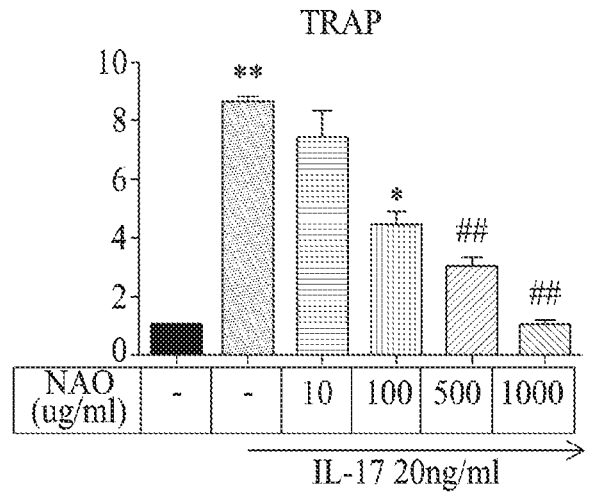
FIG. 7 shows the effect of neoagarooligosaccharide mixture (NAO) on the expression of osteoclast differentiation markers under the condition of inducing differentiation of peripheral blood mononuclear cells into osteoclasts.
Figure 7:
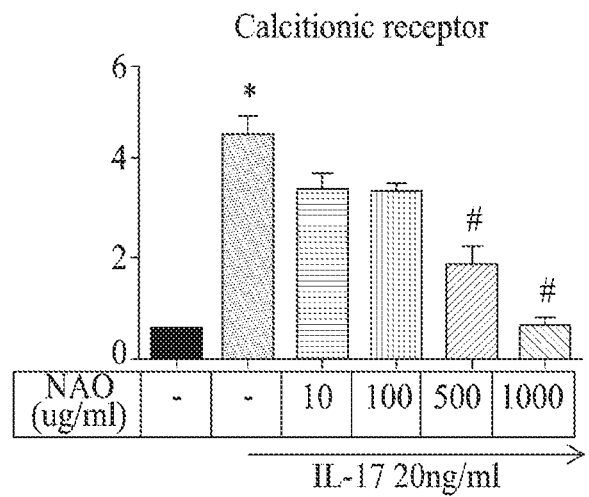
Figure 7:
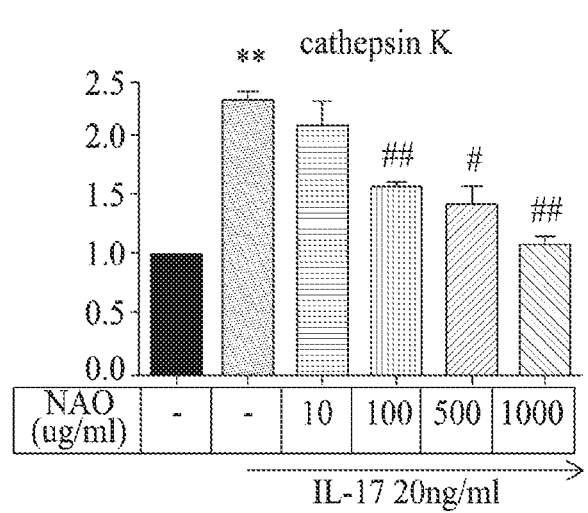

FIG. 7 shows the effect of neoagarooligosaccharide mixture (NAO) on the expression of osteoclast differentiation markers under the differentiation induction condition of peripheral blood mononuclear cells to osteoclast. As shown in FIG. 7, the neoagarooligosaccharide mixture (the partially purified DagA enzyme reaction product obtained in Example 3, NAO) was pretreated on human peripheral blood mononuclear cells so that the expressions of TRAP, calcitonin receptor and cathepsin K, which are osteoclast differentiation markers, were decreased in a concentration-dependent manner under the differentiation induction condition of peripheral blood mononuclear cells to osteoclast.

As described above, the present invention is described with reference to exemplary embodiments thereof. However, the present invention is not limited to the exemplary embodiments, and various modifications may be made therein without departing from the scope and spirit of the present invention. Therefore, the scope of protection of the present invention is not limited to the specific embodiments but should be construed as including all embodiments belonging to the accompanying claims.

The invention claimed is:

1. A method for preventing or treating arthritis or osteoporosis which is caused or progressed by a differentiation of mononuclear cells into osteoclasts, comprising:
   administering a composition to a subject in need thereof,
   wherein the composition comprises a neoagarooligosaccharide mixture as an active ingredient, and
   wherein the neoagarooligosaccharide mixture comprises neoagarobiose, neoagarotetraose, and neoagarohexaose.

2. The method of claim 1, wherein the neoagarooligosaccharide mixture comprises 1% by weight to 10% by weight of neoagarobiose, 55% by weight to 75% by weight of neoagarotetraose and 20% by weight to 40% by weight of neoagarohexaose with respect to a total weight of the neoagarooligosaccharide mixture.

3. The method of claim 1, wherein the neoagarooligosaccharide mixture is an enzyme reaction product obtained from an enzyme reaction between (i) a substrate selected from the group consisting of agar and agarose, and (ii) DagA as a beta-agarase derived from *Streptomyces coelicolor*, or a purified product of the enzyme reaction product.

4. The method of claim 1, wherein the method prevents or treats the arthritis.

5. The method of claim 1, wherein the method prevents or treats the osteoporosis.

* * * * *